United States Patent
Huang et al.

(10) Patent No.: US 10,327,624 B2
(45) Date of Patent: Jun. 25, 2019

(54) SYSTEM AND METHOD FOR IMAGE PROCESSING TO GENERATE THREE-DIMENSIONAL (3D) VIEW OF AN ANATOMICAL PORTION

(71) Applicant: SONY CORPORATION, Tokyo (JP)

(72) Inventors: Ko-Kai Albert Huang, San Jose, CA (US); Ming-Chang Liu, San Jose, CA (US); Seiji Kobayashi, Tokyo (JP); Tatsumi Sakaguchi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 226 days.

(21) Appl. No.: 15/264,824

(22) Filed: Sep. 14, 2016

(65) Prior Publication Data

US 2017/0263020 A1    Sep. 14, 2017

Related U.S. Application Data

(60) Provisional application No. 62/306,817, filed on Mar. 11, 2016.

(51) Int. Cl.

| | |
|---|---|
| *G06K 9/00* | (2006.01) |
| *A61B 1/00* | (2006.01) |
| *A61B 90/00* | (2016.01) |
| *G06T 11/00* | (2006.01) |
| *G06T 7/593* | (2017.01) |

(Continued)

(52) U.S. Cl.
CPC ...... *A61B 1/00193* (2013.01); *A61B 1/00009* (2013.01); *A61B 90/36* (2016.02); *G06T 7/11* (2017.01); *G06T 7/593* (2017.01); *G06T 11/008* (2013.01); *A61B 1/3132* (2013.01);

*A61B 2034/2065* (2016.02); *A61B 2090/367* (2016.02); *A61B 2090/3612* (2016.02);
(Continued)

(58) Field of Classification Search
None
See application file for complete search history.

(56) References Cited

U.S. PATENT DOCUMENTS

| | | | |
|---|---|---|---|
| 8,819,591 B2 | 8/2014 | Wang et al. | |
| 9,547,940 B1 * | 1/2017 | Sun | G06T 19/006 |

(Continued)

OTHER PUBLICATIONS

International Search Report and Written Opinion of PCT Application No. PCT/US2017/21335, dated May 25, 2017, 8 pages of ISRWO.

*Primary Examiner* — Atiba O Fitzpatrick
(74) *Attorney, Agent, or Firm* — Chip Law Group

(57) ABSTRACT

Various aspects of a system and method to process an image for generation of a three-dimensional (3D) view of an anatomical portion are disclosed herein. The system includes an image-processing device configured to receive a plurality of two-dimensional (2D) images associated of an anatomical portion, each with a first field-of-view (FOV) value. A first 3D view of the anatomical portion with a second FOV value, is generated from a 3D reconstruction of the anatomical portion. The 3D reconstruction is obtained by use of a set of 2D image frames selected from the received plurality of 2D images. The second FOV value is greater than the first FOV value of each of the plurality of 2D images of the anatomical portion. A second 3D view is generated, based on the alignment of the generated first 3D view with 3D data associated with a pre-operative state of the anatomical portion.

19 Claims, 4 Drawing Sheets

(51) Int. Cl.
*G06T 7/11* (2017.01)
*A61B 1/313* (2006.01)
*A61B 34/20* (2016.01)

(52) U.S. Cl.
CPC ............ *A61B 2090/371* (2016.02); *G06T 2207/10021* (2013.01); *G06T 2207/30004* (2013.01)

(56) References Cited

U.S. PATENT DOCUMENTS

| | | |
|---|---|---|
| 2014/0058406 A1 | 2/2014 | Tsekos |
| 2014/0276001 A1 | 9/2014 | Ungi et al. |
| 2014/0303491 A1* | 10/2014 | Shekhar ............... A61B 8/4209 600/424 |
| 2014/0330108 A1 | 11/2014 | Dempsey |
| 2015/0150523 A1 | 6/2015 | Sirpad et al. |
| 2015/0227679 A1 | 8/2015 | Kamer et al. |
| 2016/0008074 A1 | 1/2016 | Glossop |
| 2016/0015469 A1 | 1/2016 | Goshayesh et al. |

* cited by examiner

SYSTEM AND METHOD FOR IMAGE PROCESSING TO GENERATE THREE-DIMENSIONAL (3D) VIEW OF AN ANATOMICAL PORTION

CROSS-REFERENCE TO RELATED APPLICATIONS/INCORPORATION BY REFERENCE

This application claims priority to U.S. Provisional Patent Application Ser. No. 62/306,817 filed on Mar. 11, 2016, the entire content of which is hereby incorporated by reference.

FIELD

Various embodiments of the disclosure relate to a system and method for image processing. More specifically, various embodiments of the disclosure relate to a system and method for image processing to generate 3D view of an anatomical portion.

BACKGROUND

Recent developments in the field of medical image computing have led to advancements in various image-processing techniques, wherein the dimensionality of medical images is a critical parameter. Typically, before an image-guided operative procedure, such as Magnetic Resonance Imaging (MRI)/Computed Tomography (CT), patient (or "subject") data is acquired. During the image-guided operative procedure, the subject is positioned in an operating room (OR). Thereafter, subject alignment may be performed to bring the MRI/CT data into the surgical navigation system.

Conventional approaches, such as fiducial markers, head masks, surface tracers, anatomical landmarks, or additional MRI/CT data, are utilized to perform such subject alignment. In such cases, alignment is based on laser-assistance and/or integrated tools. Accordingly, the surface of the anatomical portion of the subject may be traced and a mask is mapped on the traced surface of the anatomical portion. However, such subject alignment performed by use of conventional approaches may not be sufficiently robust to generate high-dimensional views of the anatomical portion to be used during a surgery. Therefore, an advanced technique may be desired for quick generation of enhanced views of anatomical portions of the subject that may be used during the surgery.

Further limitations and disadvantages of conventional and traditional approaches will become apparent to one of skill in the art, through comparison of described systems with some aspects of the present disclosure, as set forth in the remainder of the present application and with reference to the drawings.

SUMMARY

A system and method for image processing to generate a three-dimensional (3D) view of an anatomical portion is provided substantially as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

DETAILED DESCRIPTION

Various implementations may be found in a system and/or a method for image processing to generate 3D view of an anatomical portion. Exemplary aspects of the disclosure may include a method to receive, by an image-processing device, a plurality of two-dimensional (2D) images associated with an intra-operative state of the anatomical portion. Each of the plurality of 2D images may have a first field-of-view (FOV) value. Based on a specified criterion, a first 3D view of the anatomical portion with a second FOV value may be generated from a 3D reconstruction of the anatomical portion. The 3D reconstruction may be obtained by use of a set of 2D image frames, selected from the received plurality of 2D images. The second FOV value of the first 3D view of the anatomical portion may be greater than the first FOV value of each of the plurality of 2D images of the anatomical portion. A second 3D view may be generated, based on alignment of the generated first 3D view with 3D data associated with a pre-operative state of the anatomical portion.

In accordance with an embodiment, the plurality of 2D images may be captured from a plurality of positions around the anatomical portion in the intra-operative state. In accordance with an embodiment, the specified criterion to select the set of 2D image frames from the received plurality of 2D images of the anatomical portion may be relative distance covered by the imaging device. The imaging device may correspond to a camera, a microscopic imager, a stereoscopic imager, and/or a laparoscopic imager. In accordance with an embodiment, the 3D reconstruction of the anatomical portion may be performed frame by frame from the set of 2D image frames selected from the received plurality of 2D images.

In accordance with an embodiment, a region-of-interest (ROI) may be extracted from the obtained 3D reconstruction of the anatomical portion. In accordance with an embodiment, a 3D pose of the anatomical portion may be estimated from the obtained 3D reconstruction of the anatomical portion and the extracted ROI.

In accordance with an embodiment, a first 3D point cloud of the generated first 3D view of the anatomical portion, in a first coordinate space, may be aligned with a second 3D point cloud of the 3D data of the anatomical portion in a second coordinate space. In accordance with an embodiment, coordinate transformation of the generated second 3D view, with respect to a surgical plan, may be based on the 3D data associated with the pre-operative state of the anatomical portion, by use of a set of transformation parameters. The 3D data associated with the pre-operative state of the anatomical portion may correspond to a Magnetic Resonance Imaging (MRI), a Computed Tomography (CT) image, or a Positron Emission Tomography (PET) scan of the anatomical portion.

Figure 1:
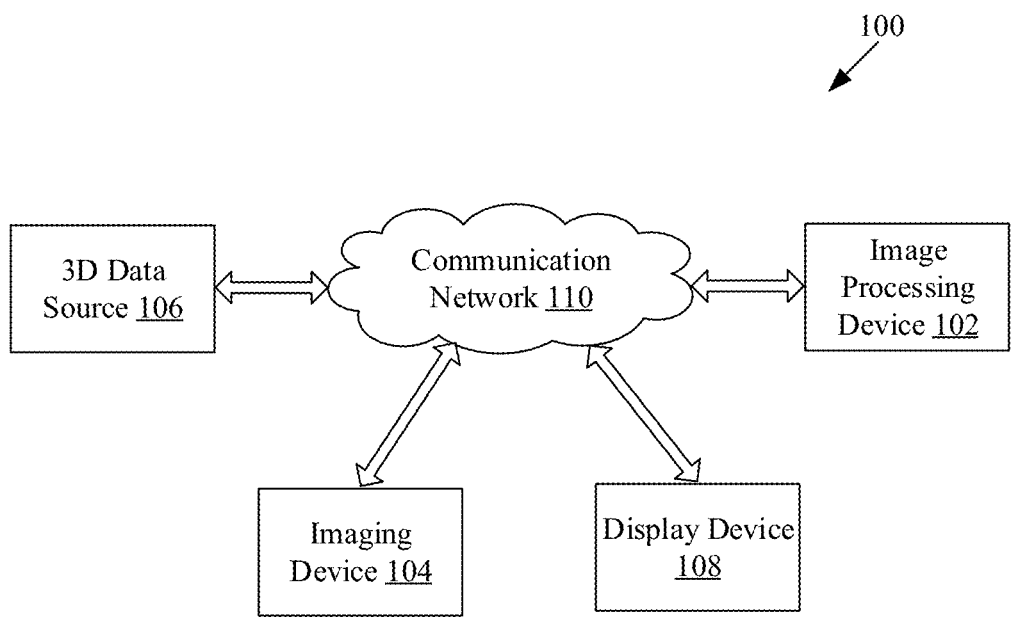
FIG. 1 is a block diagram that illustrates a system network for image processing to generate a three-dimensional (3D) view of an anatomical portion, in accordance with an embodiment of the disclosure.

FIG. 1 is a block diagram that illustrates a network diagram of a system for image processing to generate a 3D view of the anatomical portion, in accordance with an embodiment of the disclosure. With reference to FIG. 1, there is shown a network system 100. The network system 100 may include an image-processing device 102, an imaging device 104, a 3D data source 106, a display device 108, and a communication network 110. The image-processing device 102 may be communicatively coupled to the imaging device 104, the 3D data source 106, and the display device 108, via the communication network 110.

The image-processing device 102 may comprise suitable logic, circuitry, interfaces, and/or code that may be configured to receive a plurality of 2D images from the imaging device 104, via the communication network 110. The plurality of 2D images may be associated with the intra-operative state of an anatomical portion of a subject. Each of the plurality of 2D images may have a first field-of-view (FOV) value, such as a narrow FOV. The functionalities of the image-processing device 102 may be implemented in local devices (such as a medical diagnostic device or a high-speed computing device), or remote devices (such as application server or a graphical image processing server). Examples of the image-processing device 102 may include, but are not limited to, a wearable device, such as smart-glass or a head-mounted device, a computing device, a server, an augmented reality-based display device, a computer workstation, a mainframe machine, and/or other image-processing devices.

In accordance with an embodiment, the anatomical portion may be an anatomical region, and/or an organ of a subject, such as a human subject. The anatomical portion may include a plurality of heterogeneous anatomical surface structures. In accordance with an embodiment, the anatomical portion may be a brain (cranial region), or at least a portion of a brain of the human subject. In such an embodiment, the plurality of heterogeneous surface structures may be the cortex, blood vessels or arteries of the brain. The plurality of surface structures may further include a tumor structure within the brain of the human subject. In accordance with an embodiment, the anatomical portion may be a heart (cardiac region), which also include heterogeneous anatomical surface structures.

A person with ordinary skill in the art will understand that the scope of the disclosure is not limited to implementation of the disclosed system and method to assist in a surgery of the anatomical portion of the human subject. In accordance with an embodiment, the disclosed system and method may be used to assist in a surgery of anatomical portions or anatomical regions of an animal subject. Further, the disclosed system and method may also be useful to provide assistance in a surgery of anatomical portions or regions other than the brain or the heart, as discussed above.

The imaging device 104 may comprise suitable logic, circuitry, interfaces, and/or code that may be configured to capture the plurality of 2D images associated with the intra-operative state of the anatomical portion. The plurality of 2D images may be captured from a plurality of positions around the anatomical portion in the intra-operative state by the imaging device 104. The plurality of 2D images may correspond to 2D stereoscopic images with the first FOV value, such as a narrow FOV. Further, the imaging device 104 may be configured to transmit the captured plurality of 2D images to the image-processing device 102, via the communication network 110. The plurality of 2D images, such as stereo image pairs, may be acquired by use of multiple cameras from different viewpoints, multiple camera lenses of a single stereo camera, or a single moving camera. Examples of the imaging device 104 may include, but are not limited to, a camera, a microscopic imager, a stereoscopic imager, an endoscopic imager, and a laparoscopic imager. For example, the imaging device 104 may be mounted on a surgical microscope used to perform microsurgery.

The 3D data source 106 may comprise suitable logic, circuitry, interfaces, and/or code that may be configured to generate 3D data associated with the pre-operative state of the anatomical portion. The 3D data source 106 may be further configured to transmit the generated 3D data to the image-processing device 102, via the communication network 110. The 3D data associated with the pre-operative state of the anatomical portion may be aligned with the generated first 3D view, to generate the second 3D view of the anatomical portion. The 3D data, associated with the pre-operative state of the anatomical portion may correspond to the MRI, the CT, and/or the PET image of the anatomical portion. The 3D data source 106 may correspond to a magnetic resonance imaging (MRI) scanner, a server storing the 3D data, or multimodal sources that may include the MRI scanner. Examples of the multimodal sources used to obtain the 3D data associated with the pre-operative state of the anatomical portion may include, but are not limited to, a X-ray computed tomography (CT) scanner, a magnetic resonance imaging (MRI) scanner, a magnetic resonance angiography (MRA) scanner, a fluid-attenuated inversion recovery (FLAIR) based scanner, and/or a positron emission tomography (PET) scanner.

The display device 108 may comprise suitable logic, circuitry, interfaces, and/or code that may be configured to render the generated second 3D view of the anatomical portion. The display device 108 may also be configured to render the received plurality of 2D images associated with the intra-operative state of the anatomical portion. Examples of the display device 108 may include, but are not limited to, a display screen, a television (TV), a laptop, a tablet computer, a smartphone, and/or an optical head-mounted display device. In accordance with an embodiment, the image-processing device 102, the imaging device 104, and the display device 108 may be part of a computer-assisted surgical system.

The communication network 110 may include a medium through which the image-processing device 102, the imaging device 104, the 3D data source 106, and the display device 108 may communicate with each other. Examples of the communication network 110 may include, but are not limited to, the Internet, a cloud network, a Long Term Evolution (LTE) network, a Wireless Fidelity (Wi-Fi) network, a wireless personal area network (WPAN), a Wireless Local Area Network (WLAN), a Local Area Network (LAN), a wireless wide area network (WWAN), a telephone line (POTS), and/or a Metropolitan Area Network (MAN). Various devices in the network environment 100 may be operable to connect to the communication network 110, in accordance with various wired and wireless communication protocols. The network environment 100 may also be referred to as a network system 100. Examples of such wired and wireless communication protocols may include, but are not limited to, Transmission Control Protocol and Internet Protocol (TCP/IP), User Datagram Protocol (UDP), Hypertext Transfer Protocol (HTTP), Hypertext Transfer Protocol Secure (HTTPS), File Transfer Protocol (FTP), Zigbee, EDGE, infrared (IR), IEEE 802.11, 802.16, cellular communication protocols, and/or Bluetooth (BT) communication protocols.

In operation, the image-processing device 102 (or another computing device (not shown)) may be configured to receive at least a dataset associated with an anatomical portion from the MRI scanner. The dataset may include a number of 2D images that represents slice planes taken through a volume of the anatomical portion, such as slices through the skull of the human subject. The dataset may be MRI data taken prior to a surgery. The image-processing device 102 (or the other computing device) may be configured to register the received dataset associated with the anatomical portion.

In accordance with an embodiment, the image-processing device 102 may be configured to receive a plurality of datasets associated with the anatomical portion from multi-modal source. In accordance with an embodiment, to register the plurality of datasets associated with the anatomical portion from different multi-modal sources, such as the CT and the MRI, the plurality of datasets must have overlapped content. In such an embodiment, the image-processing device 102 may be configured to register the received plurality of datasets associated with the anatomical portion, based on identification of overlapped content. Based on the received one or more datasets from the MRI scanner or the multimodality sources, the image-processing device 102 (or the other computing device) may be configured to reconstruct a plurality of surface structures of the anatomical portion, based on the registration. For example, when the anatomical portion is the brain, brain surfaces structures, such as the cerebellum cortex, cerebrum cortex, brain vessels structure, and/or the ventricles, may be reconstructed.

In accordance with an embodiment, the image-processing device 102 may be configured to generate 3D data of the anatomical portion in the pre-operative state, based on a 2D-to-3D geometry processing. The 2D-to-3D geometry processing may be a mesh geometry processing or a grid geometry processing. The generated 3D data may correspond to a 3D structure (or 3D model in the pre-operative state) that may include the reconstructed plurality of surface structures. The display device 108 may be configured to display one or more views of the generated 3D data of the anatomical portion prior to the surgery. A surgeon may plan the surgery to be conducted for the anatomical portion, based on the displayed one or more views of the 3D structure of the anatomical portion. During the formulation of the surgical plan, physical models, such as organ models, vessel maps, nerve maps, muscle and tendon maps, tissue structures, or combinations thereof, can formulate a surgical strategy with optimum access paths, and safe regions that can accept intrusion by surgical tools during the surgical operation. The surgical plan may highlight areas of the operation that can pose a danger if entered, or safe areas of the planned surgery that can allow access for the surgeon (not shown).

In accordance with an embodiment, in the intraoperative state (when the surgery is performed), the imaging device 104 may be configured to capture the plurality of 2D images of the anatomical portion. The imaging device 104 may be configured to capture the plurality of 2D images from different angles at the plurality of positions, such as a multi-view imagery. In accordance with an embodiment, the imaging device 104 may be in-built in the image-processing device 102. Alternatively, in accordance with an embodiment, the imaging device 104 may not be in-built in the image-processing device 102. In such an embodiment, the imaging device 104 may be configured to transmit the captured plurality of 2D images to the image-processing device 102, via the communication network 110.

In accordance with an embodiment, the image-processing device 102 may be configured to receive the plurality of 2D images, associated with the intra-operative state of the anatomical portion, from the imaging device 104, via the communication network 110. Each of the received plurality of 2D images may have a first FOV value. The first FOV value of each of the received plurality of 2D images may be less than a pre-determined threshold value, such as a narrow FOV. The image-processing device 102 may further transmit the received plurality of 2D images to the display device 108, via the communication network 110. The display device 108 may be configured to render the plurality of 2D images, received from the image-processing device 102.

In accordance with an embodiment, the image-processing device 102 may be configured to select a set of 2D image frames from the received plurality of 2D images, based on the specified criterion. The specified criterion may correspond to a relative distance encompassed by the imaging device 104 when the plurality of 2D images are captured.

In accordance with an embodiment, the image-processing device 102 may be further configured to perform 3D reconstruction of the anatomical portion from the set of 2D image frames selected from the received plurality of 2D images based on the specified criterion. The 3D reconstruction of the anatomical portion may be performed, frame-by-frame, from the selected set of 2D image frames during the surgery. The 3D reconstruction may correspond to point set data or a 3D model of the anatomical portion.

In accordance with an embodiment, the image-processing device 102 may be further configured to extract one or more regions-of-interest (ROIs) from the obtained 3D reconstruction of the anatomical portion. The image-processing device 102 may be further configured to estimate 3D pose of the anatomical portion, based on the reconstructed 3D reconstruction of the anatomical portion and/or the extracted one or more ROIs.

Based on the estimated 3D pose of the anatomical portion, the image-processing device 102 may be further configured to reconstruct a first 3D view of the anatomical portion. The generated first 3D view of the anatomical portion may have a second FOV value, such as a wide FOV data. The second FOV value of the generated first 3D view of the anatomical portion may be greater than the first FOV value of each of the received plurality of 2D images of the anatomical portion. The image-processing device 102 may be further configured to determine a first 3D point cloud corresponding to the generated first 3D view in a first coordinate space, such as a patient coordinate space.

In accordance with an embodiment, the image-processing device 102 may further receive a second 3D point cloud corresponding to the 3D data from the 3D data source 106, via the communication network 110. The second 3D point cloud of 3D data may be associated with the pre-operative state of the anatomical portion. The second 3D point cloud corresponding to the 3D data may be in a second coordinate space, such as an image coordinate space.

In accordance with an embodiment, the image-processing device 102 may be configured to generate the second 3D view, based on aligned data sets. The aligned data sets may correspond to alignment of the generated first 3D view with the 3D data associated with the pre-operative state of the anatomical portion. The alignment may be based on alignment of the first 3D point cloud in the first coordinate space (patient coordinate space) with the second 3D point cloud of the anatomical portion in the second coordinate space (image coordinate space). The generated second 3D view of the anatomical portion may also be represented by a 3D model that may be constructed for a desired 3D output. This constructed view may be based on 3D surface rendering or sampling techniques known in the art. The 3D model may be represented by means of a 3D point cloud or a 3D surface as per user-preference.

In accordance with an embodiment, during alignment, the image-processing device 102 may be configured to perform coordinate transformation of the generated second 3D view. This may be done with respect to the surgical plan, based on the generated 3D data (or structure) associated with the pre-operative state of the anatomical portion, by use of the set of transformation parameters. Consequently, the image-processing device 102 may generate a final 3D view of the anatomical portion, which may include the generated second 3D view overlapped on 3D data of the anatomical portion, in accordance with the surgical plan provided by the surgeon. The final 3D view of the anatomical portion is a high-resolution and detailed targeted intra-operative view, based on the surgical plan provided by the surgeon.

The image-processing device 102 may be configured to render the final 3D view of the anatomical portion on an output device, such as a display screen. In accordance with an embodiment, the image-processing device 102 may be configured to transmit the generated final 3D view of the anatomical portion to the display device 108, via the communication network 110. The display device 108 may be configured to render the received final 3D view of the anatomical portion of the anatomical portion on the display screen. In accordance with an embodiment, the display screen may be integrated with the image-processing device 102 when the image-processing device 102 is a head-mounted device or a wearable device for ease of navigation during the surgery to provide assistance in a surgery of anatomical portions or other regions of human or animal body.

As discussed above, the imaging device 104 may have narrower FOV to capture sufficient data. In accordance with an embodiment, when the imaging device 104 used has a narrower FOV, such as a microscope, to capture sufficient data for accurate patient alignment, by moving the camera around, it may be difficult accurately perform patient alignment between the patient space and the MRI/CT space. Thus, the disclosed system and method automatically reconstructs a wider FOV in 3D (such as the second 3D view) using 2D stereo image input acquired by an imager, such as the imaging device 104, which may have a narrower FOV capturing sufficient and detailed data of a surface. This wider FOV in 3D (such as the second 3D view) may enable accurate patient alignment between the patient space and the MRI/CT space as alignment is most robust and successful when key uniquely identifiable feature(s) are captured by the imaging device 104. Thus, the disclosed system and method may be used to align rigid anatomical structures, such as a head in neurosurgery, or bones in orthopedic surgeries, or other surgeries requiring a rigid patient alignment. In accordance with an embodiment, alignment of soft tissues may also be made possible.

Figure 2:
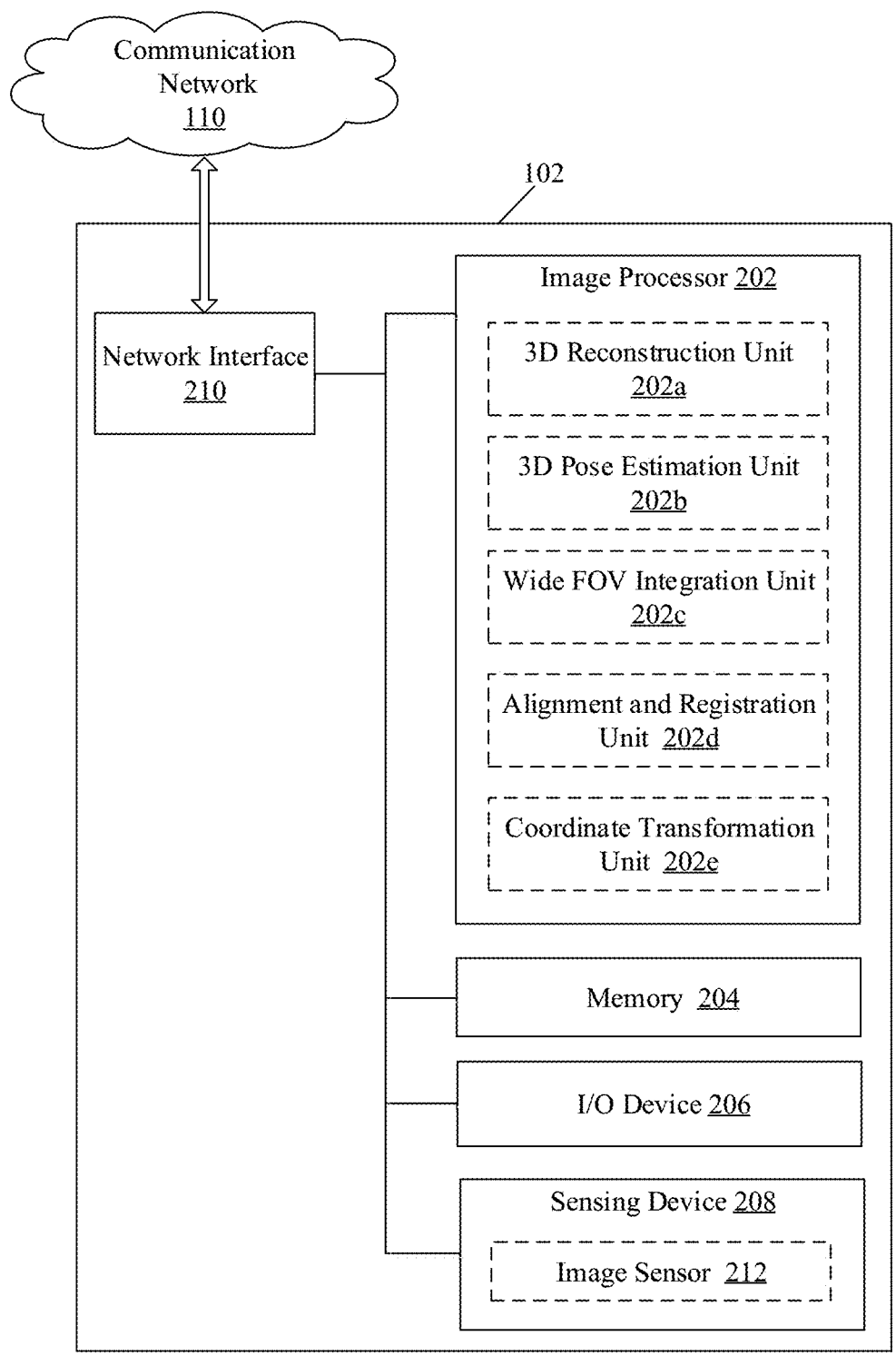
FIG. 2 is a detailed block diagram that illustrates an exemplary image-processing device that generates a 3D view of an anatomical portion, in accordance with an embodiment of the disclosure.

FIG. 2 is a block diagram that illustrates an exemplary image-processing device that generates 3D view of the anatomical portion, in accordance with an embodiment of the disclosure. FIG. 2 is explained in conjunction with elements from FIG. 1. With reference to FIG. 2, the image-processing device 102 may include an image processor 202, a memory 204, one or more input/output (I/O) devices, such as an I/O device 206, a sensing device 208, and a network interface 210. The block diagram may further include various specialized processing units, such as a 3D reconstruction unit 202a, a 3D pose estimation unit 202b, a wide FOV integration unit 202c, an alignment and registration unit 202d, and a coordinate transformation unit 202e. The sensing device 208 may further include an image sensor 212.

The image processor 202 may be communicatively coupled to the memory 204, the I/O device 206, sensing device 208, and the network interface 210. The network interface 210 may communicate with the imaging device 104, the 3D data source 106, and the display device 108, via the communication network 110, under the control of the image processor 202.

The image processor 202 may comprise suitable logic, circuitry, interfaces, and/or code that may be operable to execute a set of instructions stored in the memory 204. The image processor 202 may be configured to provide instructions to one or more specialized units to perform one or more specific operations. The image processor 202 may be further configured to perform selection of a set of 2D image frames from a plurality of 2D images, based on a specified criterion. The image processor 202 may be further configured to perform image rectification and disparity estimation of the selected set of 2D image frames. The image processor 202 may be implemented based on a number of processor technologies known in the art. Examples of the image processor 202 may be an X86-based processor, a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, a central processing unit (CPU), and/or other control circuits.

The 3D reconstruction unit 202a may comprise suitable logic, circuitry, interfaces, and/or code that may be configured to perform the 3D reconstruction of the anatomical portion from the set of 2D image frames. The 3D reconstruction unit 202a may perform 3D reconstructions based on one or more algorithms known in the art, such as Numerical Approximation algorithms and Binocular Stereo Vision algorithms.

The 3D pose estimation unit 202b may comprise suitable logic, circuitry, interfaces, and/or code that may be configured to estimate a 3D pose of the anatomical portion, based on the 3D reconstruction of the anatomical portion and the focal length of the imaging device 104. The estimation of the 3D pose of the anatomical portion may be further based on one or more ROIs extracted from the obtained 3D reconstruction of the anatomical portion. The 3D pose estimation unit 202b may estimate 3D pose, based on one or more known in the art pose estimation algorithms, such as POSIT and SolvePnP, that rely on iterative procedures and approximate projection paradigms.

The wide FOV integration unit 202c may comprise suitable logic, circuitry, interfaces, and/or code that may be configured to reconstruct a first 3D view of the anatomical portion. The first 3D view may be reconstructed based on sequential integration of transformed data sets, such as estimated 3D poses, received from the 3D pose estimation unit 202b. The wide FOV integration unit 202c may further utilize one or more techniques, such as 3D surface rendering and/or 3D sampling, to generate the 3D surface and/or the 3D point cloud in the patient coordinate space.

The alignment and registration unit 202d may comprise suitable logic, circuitry, interfaces, and/or code that may be configured to generate the second 3D view, based on alignment of the generated first 3D view with the 3D data associated with the pre-operative state of the anatomical portion. More specifically, the first 3D point cloud of the generated first 3D view in the first coordinate space may be aligned with a second 3D point cloud of 3D data of the anatomical portion in a second coordinate space. Such alignment may be based on one or more algorithms known in the art, such as shape feature selection, matching, and optimization algorithms.

The coordinate transformation unit 202e may comprise suitable logic, circuitry, interfaces, and/or code that may be configured to maintain a positional correlation between the generated second 3D view and the surgical plan, based on the 3D data received from the 3D data source 106. In other words, the coordinate transformation may be performed on generated second 3D view with respect to the surgical plan based on the 3D data associated with the pre-operative state of the anatomical portion, by use of the set of transformation parameters.

In an embodiment, the surgeon may prepare the surgical plan, based on 3D data of the anatomical portion. The surgical strategy may identify optimum egress paths and safe regions that may accept intrusion by surgical tools during the surgical operation. The surgical plan may further provide extensive details of the requirements of the surgical operation. Surgical details of the operation may comprise identification of safe areas, an entry path, location, shape and size of the anatomical portion, and danger zones, which if entered could harm the patient. The surgeon may execute the surgical plan on the anatomical portion of the patient during a surgical operation. Consequently, the coordinate transformation unit 202e may generate the final 3D view of the anatomical portion, which may include the generated second 3D view overlapped on 3D data of the anatomical portion, in accordance with the surgical plan provided by the surgeon.

With reference to FIG. 2, the one or more specialized processing units may be implemented as a separate processor or circuitry in the image-processing device 102. In an embodiment, the one or more specialized processing units and the image processor 202 may be implemented as an integrated processor or a cluster of processors that perform the functions of the one or more specialized processing units and the image processor 202, collectively. In an embodiment, the one or more specialized processing units may be implemented as a set of instructions stored in the memory 204, which upon execution by the image processor 202, may perform the functions and operations of the image-processing device 102.

The memory 204 may comprise suitable logic, circuitry, and/or interfaces that may be configured to store a machine code and/or a set of instructions executable by the image processor 202, the 3D reconstruction unit 202a, the 3D pose estimation unit 202b, the wide FOV integration unit 202c, the alignment and registration unit 202d, and the coordinate transformation unit 202e. The memory 204 may be configured to store the plurality of 2D images associated with the intra-operative state of the anatomical portion, the set of 2D image frames selected from the received plurality of 2D images, and the first FOV values to which they correspond. The memory 204 may be further configured to store specified criterion to select the set of 2D image frames, the 3D reconstruction of the anatomical portion, 3D data associated with the pre-operative state of the anatomical portion, and the generated second 3D view of the anatomical portion. The memory 204 may be further configured to store the second FOV value of the generated second 3D view of the anatomical portion, and the set of transformation parameters based on the aligned data sets. Examples of implementation of the memory 204 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The I/O device 206 may comprise suitable logic, circuitry, interfaces, and/or code that may be configured to receive an input from the one or more users, such as a surgeon or a patient. The I/O device 206 may be further configured to provide an output to the one or more users. The I/O device 206 may comprise various input and output devices that may be operable to communicate with the image processor 202. Examples of the input devices may include, but are not limited to, a touch screen, physical input buttons, a joystick, a microphone, and/or a docking station. Examples of the output devices may include, but are not limited to, an integrated display screen, a touch screen display, and/or a speaker.

The sensing device 208 may comprise suitable logic, circuitry, interfaces, and/or code that may be configured to detect/measure events or changes in biological, physical, and/or chemical parameters and provide a corresponding output, generally as an electrical or optical signal. For example, the image sensor 212 may enable the image-processing device 102 to capture the plurality of 2D images. Other examples of the sensing device 208 may include, but are not limited to, pressure sensors, temperature sensors, and humidity sensors may monitor and regulate gas flow and gas conditions in Anesthesia Machines, Respirators, and Ventilators.

The network interface 210 may comprise suitable logic, circuitry, interfaces, and/or code that may be configured to connect and communicate with an external device, such as the display device 108, via the communication network 110. The network interface 210 may implement known technologies to support wired or wireless communication with the communication network 110. The network interface 210 may include, but is not limited to, an antenna, a frequency modulation (FM) network interface, a radio frequency (RF) network interface, one or more amplifiers, a tuner, one or more oscillators, a digital signal processor, a coder-decoder (CODEC) chipset, a subscriber identity module (SIM) card, and/or a local buffer. The network interface 210 may communicate via wireless communication with networks, such as the Internet, an Intranet and/or a wireless network, such as a cellular telephone network, a wireless local area network (LAN) and/or a metropolitan area network (MAN). The wireless communication may use any of a plurality of communication standards, protocols and technologies, such as Long Term Evolution (LTE), Global System for Mobile Communications (GSM), Enhanced Data GSM Environment (EDGE), wideband code division multiple access (W-CDMA), code division multiple access (CDMA), time division multiple access (TDMA), Bluetooth, Wireless Fidelity (Wi-Fi) (i.e. 120 g, IEEE 802.11a, IEEE 802.11b, IEEE 802.11g and/or IEEE 802.11n), voice over Internet Protocol (VoIP), Wi-MAX, a protocol for email, instant messaging, and/or Short Message Service (SMS).

In operation, the image sensor 212, of the sensing device 208, may be configured to capture a plurality of 2D images (such as stereoscopic images), of a surface of an anatomical portion of a patient in an operating room (OR). The plurality of 2D images may correspond to an intra-operative state of the anatomical portion and may include multiple images of the anatomical portion captured from different angles with respect to a reference. Each of the captured plurality of 2D images may have a first FOV. The plurality of 2D images may be captured by the image sensor 212, based on an input signal received from a user, such as a nurse, a physician, and other healthcare professional. The input signal may be provided by the user, via selection of a graphical button rendered on a user interface, or a button-press event of a hardware button available at the image-processing device 102.

In accordance with an embodiment, the image processor 202, in conjunction with the network interface 210, may retrieve the plurality of 2D images from an external database (not shown), via the communication network 110. In accordance with an embodiment, the image-processing device 102, in conjunction with the network interface 210, may receive the plurality of 2D images from the imaging device 104, via the communication network 110. In such a case, the imaging device 104 may comprise one or more image sensors configured to capture the plurality of 2D images. Examples of the imaging device 104 may include, but are not limited to, the camera, the microscopic imager, the stereoscopic imager, and the laparoscopic imager.

In accordance with an embodiment, the image processor 202 may communicate the plurality of 2D images to the 3D reconstruction unit 202a. The surgeon may wish to view the set of 2D image frames at an accelerated pace. In such a case, the image processor 202 may be configured to select the set of 2D image frames from the received plurality of 2D images, based on the specified criterion for accelerated viewing. The specified criterion may correspond to the relative distance encompassed by the image sensor 212 to capture the plurality of 2D images. The image processor 202 may be further configured to perform image rectification on the selected set of 2D image frames. The image rectification includes transformation of the selected set of 2D image frames onto a common image plane (or common map coordinate system). The image rectification may facilitate identification of matching points between the selected set of 2D image frames required for subsequent 3D reconstruction. The image processor 202 may be further configured to estimate disparity in the selected set of 2D image frames that correspond to stereo images. Disparity may correspond to an apparent pixel difference or motion between a pair of stereo image frames from the rectified set of 2D image frames. The disparity estimation may facilitate the determination of disparity maps for the selected set of 2D image frames required for subsequent 3D reconstruction. The image processor 202 may communicate the matching points and disparity maps of the selected set of 2D image frames to the 3D reconstruction unit 202a.

The 3D reconstruction unit 202a may be configured to perform the 3D reconstruction of the anatomical portion from the selected set of 2D image frames, based on the matching points and disparity maps received from the image processor 202. The 3D reconstruction of the anatomical portion may be performed, frame-by-frame, from the selected set of 2D image frames. The 3D reconstruction of the anatomical portion may be performed based on one or more algorithms known in the art, such as the Numerical Approximation Algorithm. The 3D reconstruction unit 202a may be configured to communicate the obtained 3D reconstruction of the anatomical portion to the image processor 202. In accordance with an embodiment, the 3D reconstruction unit 202a, in conjunction with the image processor 202, may be configured to determine one or more incorrect, outlier, and/or noisy frames/data from the obtained 3D reconstruction. The 3D reconstruction unit 202a may be configured to communicate the noise-free 3D reconstruction of the anatomical portion to the 3D pose estimation unit 202b.

In accordance with an embodiment, the image processor 202 may be configured to extract an ROI from the obtained 3D reconstruction of the anatomical portion. The image processor 202 may be configured to perform 2D tracking to determine a set of 2D features, such as optical flow of a plurality of pixels, in the extracted ROI of the 3D reconstruction of the anatomical portion. The image processor 202 may be configured to communicate the determined 2D features to the 3D pose estimation unit 202b.

In accordance with an embodiment, the 3D pose estimation unit 202b may be further configured to estimate 3D pose of the extracted ROI of the anatomical portion. The 3D pose estimation may be performed based on the 2D features determined by the image processor 202 and the noise-free 3D reconstruction generated by the 3D reconstruction unit 202a.

In accordance with an embodiment, the 3D pose may be estimated by the determined 2D features mapped on 3D coordinates of the 3D reconstruction, via known techniques, such as RANdom SAmple Consensus (RANSAC) algorithm, based on the predetermined models that are based on physical structure of the anatomical portion. In accordance with an embodiment, the RANSAC algorithm may be utilized to remove outlying matches that do not fit with 3D rigid transformations (such as rotation, translation, or other transformation assumptions). The RANSAC algorithm is a non-deterministic iterative method for estimation of parameters of a mathematical model from a set of observed data, which contains the outliers. In accordance with an embodiment, the RANSAC algorithm may be modified based on error check of frame-model registration. The 3D pose estimation unit 202b may communicate the estimated 3D pose to the wide FOV integration unit 202c.

In accordance with an embodiment, the wide FOV integration unit 202c may be configured to generate a first 3D view of the anatomical portion, based on the 3D pose estimation of the extracted ROI of the anatomical portion. The first 3D view may be generated based on sequential integration of transformed data sets, such as estimated 3D poses, received from the 3D pose estimation unit 202b. The wide FOV integration unit 202c may be further configured to determine a 3D surface and/or a 3D point cloud of the first 3D view of the anatomical portion. The generated first 3D view of the anatomical portion may have a second FOV value, such as a wide FOV with greater details. The second FOV value of the generated first 3D view of the anatomical portion may be greater than the first FOV value of each of the received plurality of 2D images of the anatomical portion. The wide FOV integration unit 202c may further utilize one or more techniques, such as 3D surface rendering and/or 3D sampling, to generate the 3D surface and/or the 3D point cloud (or the first 3D point cloud) in patient coordinate space. The wide FOV integration unit 202c may communicate the 3D point cloud in patient coordinate space to the alignment and registration unit 202d.

In accordance with an embodiment, the alignment and registration unit 202d, in conjunction with the image processor 202, may be align the 3D point cloud of the generated first 3D view (intra-operative state) in the patient coordinate space with another 3D point cloud corresponding to the 3D data (pre-operative state) of the anatomical portion in an image coordinate space. The image processor 202 may be configured to receive the 3D point cloud of the 3D data of the anatomical portion in an image coordinate space from external devices, such as an MRI or a CT scan device. The 3D data, which corresponds to the MRI or the CT data of the anatomical portion, may be associated with the pre-operative state of the anatomical portion. Such alignment may be based on one or more algorithms known in the art, such as shape feature selection, matching, and optimization algorithms. The generated second 3D view of the anatomical portion may also be represented by a 3D model that may be constructed for a desired 3D output, based on 3D surface rendering or sampling techniques known in the art.

In accordance with an embodiment, a point registration module in the alignment and registration unit 202d may perform refinement, as needed, to further align the 3D point cloud of the generated first 3D view and the 3D point cloud of the 3D data. Based on the alignment of the 3D point cloud of the generated first 3D view in the patient coordinate space with the 3D point cloud of the 3D data of the anatomical portion in the image coordinate space, the alignment and registration unit 202d may be configured to generate a second 3D view of the anatomical portion and an associated aligned data set. The second 3D view may be associated with one or more transformation parameters. The alignment and registration unit 202d may communicate the one or more transformation parameters and/or the generated second 3D view of the anatomical portion to the coordinate transformation unit 202e.

The coordinate transformation unit 202e may collectively process the second 3D view of the anatomical portion, the surgical plan, and a historic 3D data, such as the 3D data from the pre-operation medical scan, to automatically align the historic 3D data based on the second 3D view. More specifically, the coordinate transformation unit 202e, in conjunction with the image processor 202, may perform coordinate transformation of a point cloud associated with the aligned data set with respect to two 3D point clouds. One point cloud corresponds to an historic 3D point cloud of the 3D data, which is the historic image data of the anatomical portion in the second coordinate space. The historic 3D point cloud may represent the outer layer of the skin that covers the area of the intended access of the surgical plan. The historic 3D data may be captured up to several days prior to a scheduled surgical operation represented by the surgical plan. Consequently, the coordinate transformation unit 202e may generate the final 3D view of the anatomical portion, which includes the generated second 3D view overlapped on the 3D data of the anatomical portion, in accordance with the surgical plan provided by the surgeon. The final 3D view may be associated with metadata, such as patient-aligned information. The final 3D view may be coupled to an augmented reality (AR) display managed by the image processor 202. The current surface image of the final 3D view may be coupled to the augmented reality display to establish a patient coordinate space in which the final 3D view, which may be displayed by the image processor 202.

In accordance with an embodiment, the image processor 202 may include one or more AR tags to one or more portions of the final 3D view of the anatomical portion. The image processor 202 may further perform tracking of surgical tools in the final view during the surgical procedure. In accordance with an embodiment, the final 3D view may be in position correlation with the second 3D view, which allows the AR display to present the actual position of the surgical tools used to execute the surgical plan in real time. The image processor 202 may further perform real-time analysis and provide medical and/or diagnostic recommendations based on the final 3D view of the anatomical portion of the patient.

Figure 3:
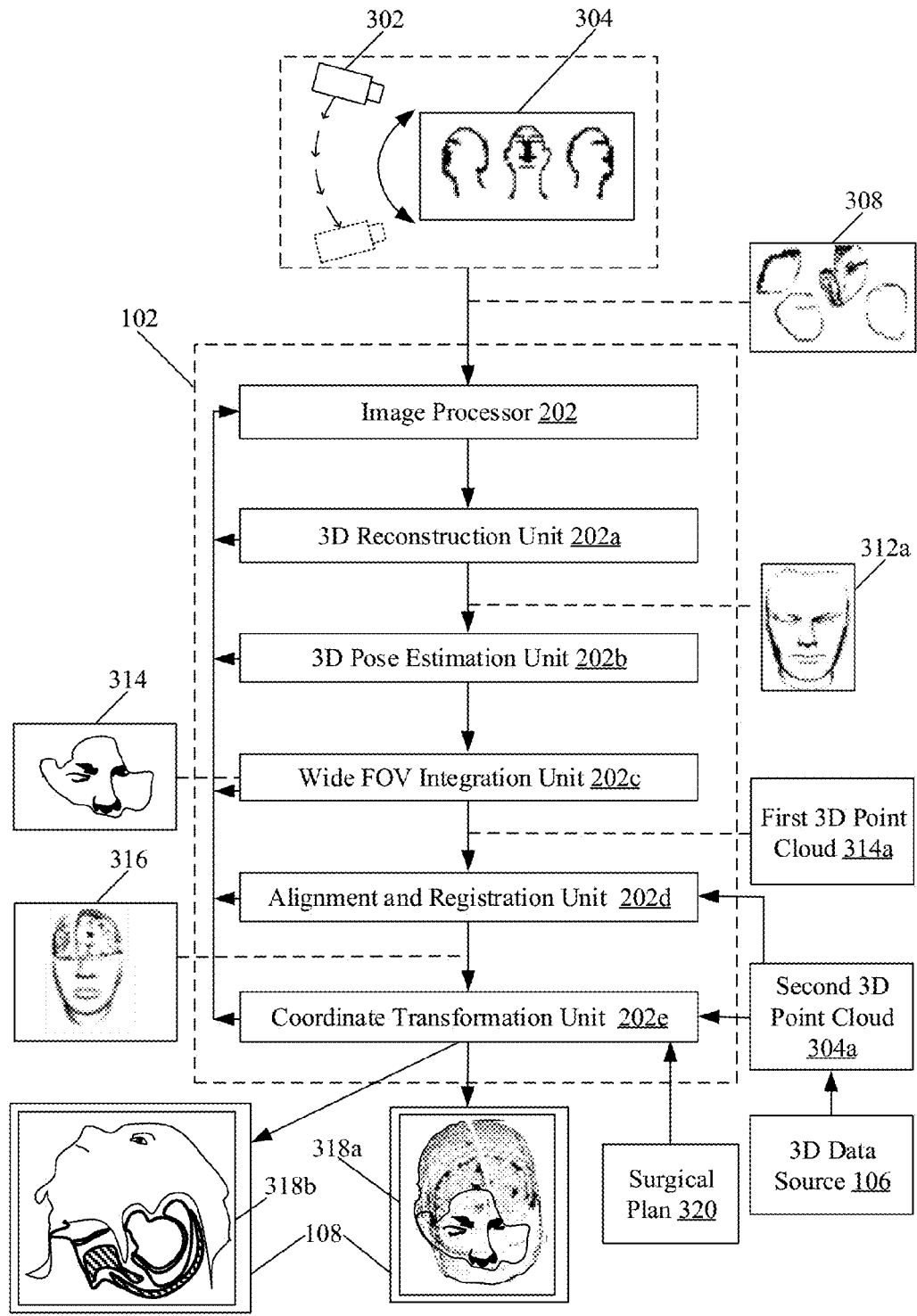
FIG. 3 is a detailed block diagram that illustrates an exemplary scenario for implementation of the disclosed system and method for image processing to generate a 3D view of an anatomical portion, in accordance with an embodiment of the disclosure.

FIG. 3 is a detailed block diagram that illustrates an exemplary scenario for implementation of the disclosed system and method for image-processing to generate a 3D view of the anatomical portions, in accordance with an embodiment of the disclosure. FIG. 3 is explained in conjunction with elements from FIG. 1, and FIG. 2. With reference to FIG. 3, there is shown a stereoscopic camera 302 at multiple positions. The stereoscopic camera 302 may correspond to the imaging device 104 (FIG. 1). The block diagram further illustrates the various devices and one or more specialized units, as explained in FIGS. 1 and 2. The image-processing device 102 may be communicatively coupled to the stereoscopic camera 302, the 3D data source 106, and the display device 108, via a communication network 110.

In operation, prior to an image-guided operative procedure of an anatomical portion, such as a cephalic region 304, the MRI, CT, and/or PET scan of the anatomical portion is performed. Based on results of the scanning techniques, pre-operative 3D data may be acquired and stored in the 3D data source 106. Further, a surgeon may utilize the pre-operative 3D data to prepare a surgical plan 320, which will be executed during the image-guided operative procedure on the cephalic region 304.

The pre-operative 3D data may be further utilized to determine the historic 3D point cloud of a surface-of-interest extracted from the pre-operative 3D data. Such historic 3D point cloud may represent the outer layer of the skin that covers the area of the surface-of-interest, on which access is intended in accordance with the surgical plan 320. The surgical plan 320 may indicate safe zones and danger zones in the surface of interest that may assist the surgeon in performance of the image-guided operative procedure. The pre-operative 3D data may be captured up to several days prior to a scheduled image-guided operative procedure represented by the surgical plan 320.

During the image-guided operative procedure, the patient is in a fixed surgery position, which may be a substantially different position than the position used to capture the pre-operative 3D data. The stereoscopic camera 302 may be configured to capture a plurality of 2D images 308, associated with the intra-operative state of the cephalic region 304 of the patient. The stereoscopic camera 302 may be configured to revolve around the cephalic region 304 to capture the plurality of 2D images 308 from different positions at different angles with respect to a reference. Each of the captured plurality of 2D images 308 may be associated with the intra-operative state of the cephalic region 304, which has a first FOV value. The stereoscopic camera 302 may further transmit the captured plurality of 2D images 308 to the image-processing device 102, via the communication network 110. The image-processing device 102 may further transmit the received plurality of 2D images to the display device 108, via the communication network 110. The display device 108 may be configured to render the plurality of 2D images, received from the image-processing device 102.

The image processor 202, in conjunction with the network interface 210, may receive the plurality of 2D images 308 from the stereoscopic camera 302, and may select a set of 2D image frames 310 from a plurality of 2D images 308, based on a specified criterion. The specified criterion may correspond to the relative distance encompassed by the stereoscopic camera 302 to capture the plurality of 2D images 308. The image processor 202 may be further configured to perform image rectification on the selected set of 2D image frames 310. The image rectification includes transformation of the selected set of 2D image frames 310 onto a common map coordinate system. The image rectification may facilitate identification of matching points between the selected set of 2D image frames 310 required for subsequent 3D reconstruction. The image processor 202 may be further configured to estimate disparity in the selected set of 2D image frames 310 that correspond to stereo images. Disparity may correspond to an apparent pixel difference or motion between a pair of stereo image frames from the rectified selected set of 2D image frames 310. The disparity estimation may facilitate determination of disparity maps for the selected set of 2D image frames 310 required for subsequent reconstruction of 3D reconstruction. The image processor 202 may communicate the matching points and disparity maps of the selected set of 2D image frames 310 to the 3D reconstruction unit 202a.

The 3D reconstruction unit 202a may be configured to perform the 3D reconstruction 312 of the cephalic region 304 from the selected set of 2D image frames 310, based on the matching points and disparity maps received from the image processor 202. The 3D reconstruction unit 202a may be configured to communicate the obtained 3D reconstruction 312 to the image processor 202. In accordance with an embodiment, the 3D reconstruction unit 202a, in conjunction with the image processor 202, may be configured to determine one or more incorrect, outlier, and/or noisy frames from the obtained 3D reconstruction. The 3D reconstruction unit 202a may be configured to communicate a noise-free 3D reconstruction 312a to the 3D pose estimation unit 202b.

In accordance with an embodiment, the image processor 202 may be configured to extract an ROI from the 3D reconstruction of the cephalic region 304. The ROI is extracted to identify the detail of the surface and algorithmically remove undesired regions, such as hair, from the surface of the ROI. In an embodiment, the image processor 202 may generate a current 3D point cloud for the extracted ROI. The image processor 202 may be configured to perform 2D tracking to determine the set of 2D features, such as optical flow of a plurality of pixels, in the extracted ROI of the obtained 3D reconstruction of the cephalic region 304. The image processor 202 may be configured to communicate the determined 2D features to the 3D pose estimation unit 202b.

In accordance with an embodiment, the 3D pose estimation unit 202b may be further configured to estimate a 3D pose of the extracted ROI of the cephalic region 304. The 3D pose estimation may be performed based on the 2D features determined by the image processor 202 and the noise-free 3D reconstruction 312a obtained by the 3D reconstruction unit 202a. The 3D pose estimation unit 202b may communicate the estimated 3D pose to the wide FOV integration unit 20c.

In accordance with an embodiment, the wide FOV integration unit 202c may be configured to reconstruct a first 3D view 314 of the cephalic region 304, based on the 3D pose estimation of the extracted ROI of the cephalic region 304. The first 3D view 314 may be reconstructed based on sequential integration of transformed data sets, such as estimated 3D poses, received from the 3D pose estimation unit 202b. The wide FOV integration unit 202c may be further configured to determine a first 3D surface and/or a first 3D point cloud 314a of the first 3D view 314 of the cephalic region 304. The generated first 3D view 314 of the cephalic region 304 may have a second FOV value. The second FOV value of the generated first 3D view 314 of the cephalic region 304 may be greater than the first FOV value of each of the received plurality of 2D images 308 of the cephalic region 304. The wide FOV integration unit 202c may further utilize one or more techniques, such as 3D surface rendering and/or 3D sampling, to generate the first 3D surface and/or the first 3D point cloud 314a in the patient coordinate space. The wide FOV integration unit 202c may communicate the first 3D point cloud 314a in patient coordinate space to the alignment and registration unit 202d.

In accordance with an embodiment, the alignment and registration unit 202d, in conjunction with the image processor 202, may perform feature-by-feature alignment of the first 3D point cloud 314a of the generated first 3D view 314 with a second 3D point cloud 304a of the pre-operative 3D data of the cephalic region 304. The first 3D point cloud 314a may be in the patient coordinate space and the second 3D point cloud 304a may be in the image coordinate space.

The alignment and registration unit 202d may be configured to receive the second 3D point cloud 304a of the 3D data of the cephalic region 304 in an image coordinate space from external devices, such as an MRI or a CT scan device. The pre-operative 3D data, which corresponds to the MRI or the CT data of the cephalic region 304, may be associated with the pre-operative state of the cephalic region 304. Such an alignment may be based on one or more known in the art algorithms, such as shape feature selection, matching, and optimization algorithms.

In accordance with an embodiment, a point registration module in the alignment and registration unit 202d may perform refinement, as needed, to further align the first 3D point cloud 314a of the generated first 3D view 314 and the second 3D point cloud 304a of the pre-operative 3D data. Based on the alignment of the first 3D point cloud 314a of the generated first 3D view 314 in the patient coordinate space with the 3D point cloud of the 3D data of the cephalic region 304 in the image coordinate space, the alignment and registration unit 202d may be configured to generate a second 3D view 316 of the cephalic region 304 and an associated aligned data set. The second 3D view may be associated with one or more transformation parameters.

The alignment and registration unit 202d may determine 3D transformation parameters, such as translation, rotation and scaling, which may align the second 3D point cloud 304a with the first 3D point cloud 314a. The second 3D view 316 may include the transformation information that may be required to position the pre-operative 3D data in the proper alignment to coincide with the current point cloud that corresponds to the extracted ROI. Accordingly, the actual position of the cephalic region 304 of the patient may be indicated.

The second 3D view 316 may also be represented by a 3D model that may be constructed for a desired 3D output, based on 3D surface rendering or sampling techniques known in the art. The alignment and registration unit 202d may communicate the one or more transformation parameters and/or the generated second 3D view 316 of the cephalic region 304 to the coordinate transformation unit 202e.

The coordinate transformation unit 202e applies the transformation parameters, such as translation, rotation, and scaling, from the second 3D view 316 and the surgical plan 320 to the pre-operative 3D data. The coordinate transformation unit 202e may merge highlighted information from the surgical plan 320, with the pre-operative 3D data to provide a final 3D view 318a that may be coupled to the AR display. The coordinate transformation unit 202e may also be configured to provide various representations of the final 3D view 318a, such as another final 3D view 318b. The coordinate transformation unit 202e maintains the positional correlation between the second 3D view 316 and the surgical plan 320, based on the pre-operative 3D data. The coordinate transformation unit 202e may provide continuous updates to the final 3D view 318a and 318b without manual intervention.

In accordance with an embodiment, the image processor 202 may include one or more AR tags to one or more portions of the final 3D view 318a and 318b of the cephalic region 304. The image processor 202 may further perform tracking of surgical tools in the final 3D view 318a and 318b during the surgical procedure. In accordance with an embodiment, the final 3D view 318a and 318b may be in position correlation with the second 3D view 316, which allows the AR display to present the actual position of the surgical tools used to execute the surgical plan 320 in real time. The image processor 202 may further perform real-time analysis and provide medical and/or diagnostic recommendations, based on the final 3D view 318a and 318b of the cephalic region 304 of the patient.

Figure 4:
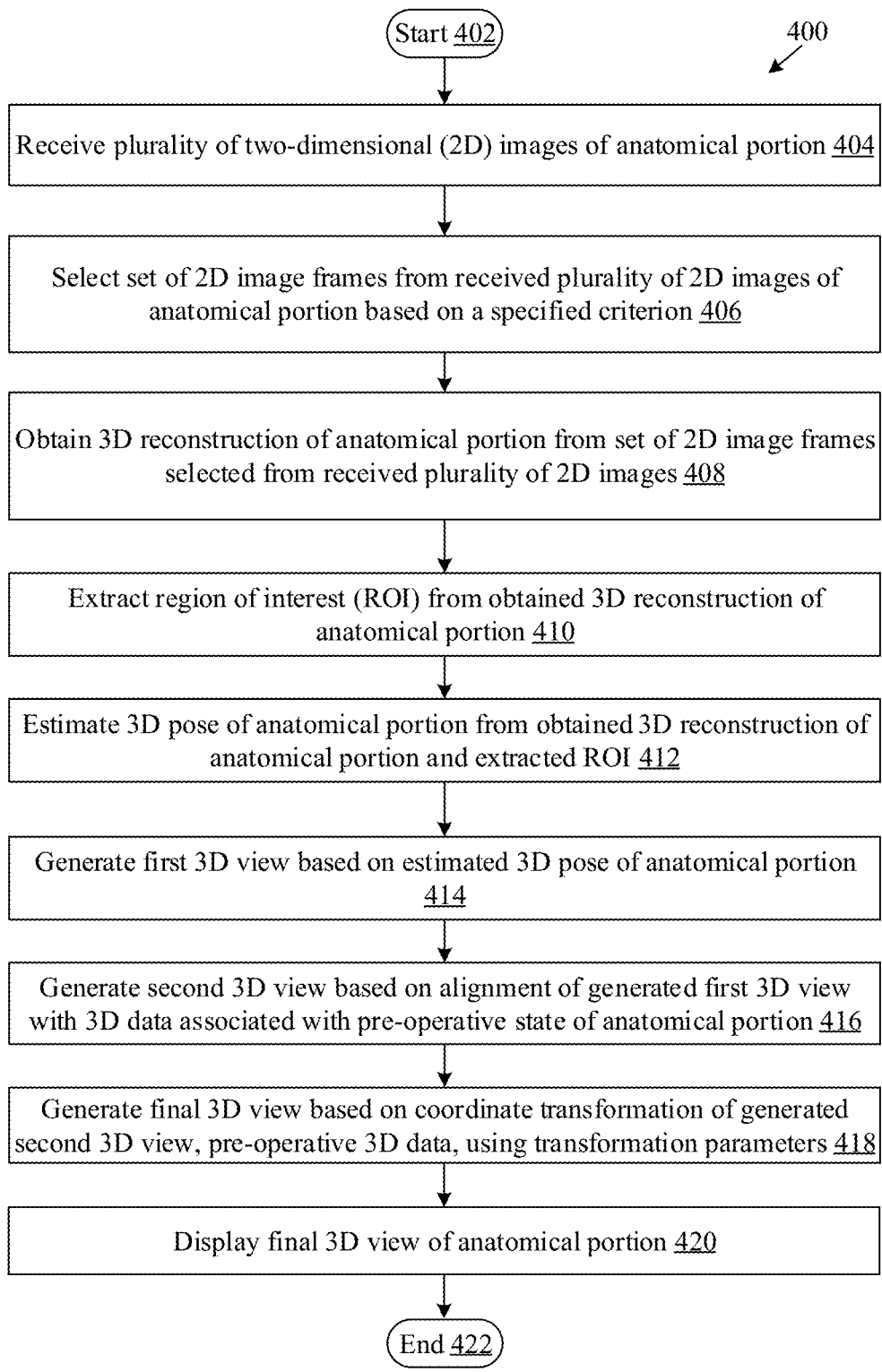
FIG. 4 is a flowchart that illustrates an exemplary method for image processing to generate a 3D view of an anatomical portion, in accordance with an embodiment of the disclosure.

FIG. 4 is a flowchart that illustrates a method for image processing to generate 3D view of the anatomical portion, in accordance with an embodiment of the disclosure. With reference to FIG. 4, there is shown a flowchart 400. The flowchart 400 is described in conjunction with FIG. 1, FIG. 2, and FIG. 3. The method, implemented at the image-processing device 102, starts at 402 and proceeds to 422.

At 404, a plurality of 2D images associated with an intra-operative state of an anatomical portion may be received by the image-processing device 102, via the communication network 110. The plurality of 2D images associated with the intra-operative state of the anatomical portion may be received by the image-processing device 102 from the image sensor 212 of the sensing device 208. Each of the received plurality of 2D images may have a first FOV value. At 406, a set of 2D image frames may be selected by the image processor 202, from the received plurality of 2D images of the anatomical portion based on a specified criterion.

At 408, a 3D reconstruction of the anatomical portion may be obtained by the 3D reconstruction unit 202a, from the set of 2D image frames selected from the received plurality of 2D images. At 410, a ROI may be extracted from the obtained 3D reconstruction of the anatomical portion, via the image processor 202.

At 412, a 3D pose of the anatomical portion may be estimated from the obtained 3D reconstruction of the anatomical portion and the extracted ROI, by the 3D pose estimation unit 202b. At 414, based on the estimated 3D pose, a first 3D view may be generated by the wide FOV integration unit 202c. The generated first 3D view of the anatomical portion may have a second FOV value, such as a wide FOV. The second FOV value of the generated first 3D view of the anatomical portion may be greater than the first FOV value of each of the received plurality of 2D images of the anatomical portion.

At 416, based on alignment of the generated first 3D view with 3D data associated with the pre-operative state of the anatomical portion, a second 3D view may be generated by the alignment and registration unit 202d. More specifically, the first 3D point cloud of the obtained 3D reconstruction in the first coordinate space may be aligned with the second 3D point cloud of the 3D data of the anatomical portion in the second coordinate space.

At 418, a final 3D view of the anatomical portion may be generated by the coordinate transformation unit 202e, based on coordinate transformation of the generated second 3D view on the 3D data of the anatomical portion with respect to the surgical plan provided by the surgeon and the pre-operative 3D data, by use of one or more transformation parameters. At 420, the final 3D view of the anatomical portion may be displayed by use of the display device 108 managed by the image processor 202. The control passes to the end 422.

In accordance with an embodiment of the disclosure, a system for image processing to generate 3D view may comprise one or more circuits configured to receive, via an image-processing device 102, a plurality of 2D images associated with an intra-operative state of an anatomical portion, each with a first FOV value, from an imaging device 104. A first 3D view of the anatomical portion with a second FOV value may be generated by one of the specialized processing units, a wide FOV integration unit 202c, in the image-processing device 102. The first 3D view may be generated from a 3D reconstruction, obtained by use of a set of 2D image frames selected from the received plurality of 2D images based on a specified criterion by a 3D reconstruction unit 202a. The second FOV value of the first 3D view of the anatomical portion may be greater than the first FOV value of each of the plurality of 2D images of the anatomical portion. Further, a second 3D view may be generated by an alignment and registration unit 202d of the image-processing device 102, based on alignment of the generated first 3D view with 3D data associated with a pre-operative state of the anatomical portion.

The imaging device 104 may have narrower FOV to capture sufficient data. In accordance with an embodiment, when the imaging device 104 used has a narrower FOV, such as a microscope, to capture sufficient data for accurate patient alignment, by moving the camera around, it may be difficult accurately perform patient alignment between the patient space and the MRI/CT space. Thus, the disclosed system and method automatically and in a faster computation time reconstructs a wider FOV in 3D (such as the generated second 3D view) using 2D stereo image input acquired by an imager, such as the imaging device 104, which may have a narrower FOV capturing sufficient and detailed data of a surface. This wider FOV in 3D (such as the second 3D view) may enable accurate patient alignment between the patient space and the MRI/CT space as alignment is most robust and successful when key uniquely identifiable feature(s) are captured by the imaging device 104.

Subject alignment performed by use of conventional approaches may not be sufficiently robust to generate high-dimensional views of the anatomical portion to be used during a surgery. Thus, the disclosed system and method provides improved technique for generation of enhanced views of anatomical portions of the subject in a faster computation time that may be used during the surgery. An improvement in the technology of digital image processing, image-capturing, and 3D visualization applied in the field of medical devices and computer-assisted surgery is provided as a result of the quick generation of enhanced views of anatomical portions of the subject during surgery. The disclosed system and method may be used to accurately align rigid anatomical structures, such as a head in neurosurgery, or bones in orthopedic surgeries, or other surgeries requiring a rigid patient alignment. In accordance with an embodiment, alignment of soft tissues may also be performed by the disclosed system and method.

Various embodiments of the disclosure may provide a non-transitory, computer readable medium and/or storage medium, and/or a non-transitory machine readable medium and/or storage medium stored thereon, a machine code and/or a computer program with at least one code section executable by a machine and/or a computer for image processing to generate 3D view. The at least one code section may cause the machine and/or computer to perform the steps that comprise receiving, by an image-processing device, a plurality of 2D images associated with an intra-operative state of an anatomical portion, each with a first FOV value, from an imaging device. A first 3D view of the anatomical portion with a second FOV value may be reconstructed by the image-processing device. The first 3D view may be generated from a 3D reconstruction, obtained by use of a set of 2D image frames selected from the received plurality of 2D images based on a specified criterion. The second FOV value of the first 3D view of the anatomical portion may be greater than the first FOV value of each of the plurality of 2D images of the anatomical portion. Further, a second 3D view may be generated by the image-processing device, based on alignment of the generated first 3D view with 3D data associated with a pre-operative state of the anatomical portion.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted to carry out the methods described herein may be suited. A combination of hardware and software may be a general-purpose computer system with a computer program that, when loaded and executed, may control the computer system such that it carries out the methods described herein. The various operations performed by the computer system may improve the functioning of the computer system itself and enable accurate, robust and successful patient alignment between the patient space and the MRI/CT space. The present disclosure may be realized in hardware that comprises a portion of an integrated circuit that also performs other functions.

The present disclosure may also be embedded in a computer program product, which comprises all the features that enable the implementation of the methods described herein, and which when loaded in a computer system is able to carry out these methods. Computer program, in the present context, means any expression, in any language, code or notation, of a set of instructions intended to cause a system with information processing capability to perform a particular function either directly, or after either or both of the following: a) conversion to another language, code or notation; b) reproduction in a different material form.

While the present disclosure has been described with reference to certain embodiments, it will be understood by those skilled in the art that various changes may be made and equivalents may be substituted without departure from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. An image processing system, comprising:
   an imaging device configured to capture a plurality of two-dimensional (2D) images; and
   an image-processing device that includes:
      at least one processor configured to:
         receive said plurality of 2D images from said imaging device,
            wherein said plurality of 2D images is associated with an intra-operative state of an anatomical portion;
         select a set of 2D image frames from said received plurality of 2D images, based on a relative distance covered by said imaging device for said capture of said plurality of 2D images;
         obtain a 3D reconstruction of said anatomical portion based on said selected set of 2D image frames;
         generate a first three-dimensional (3D) view of said anatomical portion based on said obtained 3D reconstruction of said anatomical portion; and
         generate a second 3D view of said anatomical portion based on an alignment of said generated first 3D view with 3D data associated with a pre-operative state of said anatomical portion.

2. The image processing system according to claim 1, wherein said plurality of 2D images are captured from a plurality of positions around said anatomical portion in said intra-operative state.

3. The image processing system according to claim 1, wherein said 3D reconstruction of said anatomical portion is obtained frame by frame from said selected set of 2D image frames.

4. The image processing system according to claim 1, wherein said at least one processor is further configured to extract a region-of-interest (ROI) from said 3D reconstruction of said anatomical portion.

5. The image processing system according to claim 4, wherein said at least one processor is further configured to estimate a 3D pose of said anatomical portion, based on said 3D reconstruction of said anatomical portion and said extracted ROI.

6. The image processing system according to claim 1, wherein said at least one processor is further configured to align a first 3D point cloud of said generated first 3D view of said anatomical portion in a first coordinate space with a second 3D point cloud associated with said 3D data of said anatomical portion in a second coordinate space.

7. The image processing system according to claim 6, wherein said at least one processor is further configured to transform coordinates of said generated second 3D view with respect to a surgical plan based on said 3D data associated with said pre-operative state of said anatomical portion, by a set of transformation parameters.

8. The image processing system according to claim 1, wherein said 3D data associated with said pre-operative state of said anatomical portion corresponds to one of a Magnetic Resonance Imaging (MRI) or a Computed Tomography (CT) image of said anatomical portion.

9. The image processing system according to claim 1, wherein said at least one processor is further configured to control a display device to display said second 3D view of said anatomical portion.

10. The image processing system according to claim 1, wherein said imaging device corresponds to one of a camera, a microscope imager, a stereoscopic imager, or a laparoscopic imager.

11. An image processing method, comprising:
receiving, by at least one processor of an image-processing device, a plurality of two-dimensional (2D) images captured by an imaging device,
wherein said plurality of 2D images is associated with an intra-operative state of an anatomical portion;
selecting, by said at least one processor, a set of 2D image frames from said received plurality of 2D images, based on a relative distance covered by said imaging device for said capture of said plurality of 2D images;
obtaining, by said at least one processor, a 3D reconstruction of said anatomical portion based on said selected set of 2D image frames;
generating, by said at least one processor, a first three-dimensional (3D) view of said anatomical portion based on said obtained 3D reconstruction of said anatomical portion; and
generating, by said at least one processor, a second 3D view of said anatomical portion based on an alignment of said generated first 3D view with 3D data associated with a pre-operative state of said anatomical portion.

12. The image processing method according to claim 11, wherein said plurality of 2D images are captured from a plurality of positions around said anatomical portion in said intra-operative state.

13. The image processing method according to claim 11, further comprising extracting, by said at least one processor, a region-of-interest (ROI) from said 3D reconstruction of said anatomical portion.

14. The image processing method according to claim 13, further comprising estimating, by said at least one processor, a 3D pose of said anatomical portion, based on said 3D reconstruction of said anatomical portion and said extracted ROI.

15. The image processing method according to claim 11, further comprising aligning, by said at least one processor, a first 3D point cloud of said generated first 3D view of said anatomical portion in a first coordinate space with a second 3D point cloud of said 3D data of said anatomical portion in a second coordinate space.

16. The image processing method according to claim 15, further comprising transforming, by said at least one processor, coordinates of said generated second 3D view with respect to a surgical plan based on said 3D data associated with said pre-operative state of said anatomical portion, by a set of transformation parameters.

17. The image processing method according to claim 11, wherein said 3D data associated with said pre-operative state of said anatomical portion corresponds to one of a Magnetic Resonance Imaging (MRI) or a Computed Tomography (CT) image of said anatomical portion.

18. The image processing method according to claim 11, further comprising controlling, by said at least one processor, a display device to display said second 3D view of said anatomical portion.

19. The image processing system according to claim 1, wherein
each of said plurality of 2D images has a first field-of-view (FOV) value, wherein said first FOV value is associated with a first field-of-view of said imaging device;
said first 3D view of said anatomical portion has a second FOV value,
wherein said second FOV value is associated with a second field-of-view of said image processing device; and
said second FOV value of said first 3D view is greater than said first FOV value of each of said plurality of 2D images.

* * * * *